US009440099B2

(12) United States Patent
De Ambrosi

(10) Patent No.: US 9,440,099 B2
(45) Date of Patent: Sep. 13, 2016

(54) PROCESS FOR THE PURIFICATION OF HEPARAN SULFATE AND USE THEREOF IN COSMETOLOGICAL AND DERMATOLOGICAL PREPARATIONS

(75) Inventor: Luigi De Ambrosi, Santhia (IT)

(73) Assignee: LABORATORI DERIVATI ORGANICI SPA, Milan (IT)

( * ) Notice: Subject to any disclaimer, the term of this patent is extended or adjusted under 35 U.S.C. 154(b) by 542 days.

(21) Appl. No.: 13/129,030

(22) PCT Filed: Sep. 29, 2009

(86) PCT No.: PCT/EP2009/062582
§ 371 (c)(1),
(2), (4) Date: Jul. 28, 2011

(87) PCT Pub. No.: WO2010/057710
PCT Pub. Date: May 27, 2010

(65) Prior Publication Data
US 2011/0288047 A1    Nov. 24, 2011

(30) Foreign Application Priority Data

Nov. 20, 2008 (EP) ..................................... 08169547

(51) Int. Cl.
| | | |
|---|---|---|
| *A61K 31/727* | (2006.01) | |
| *A61K 31/70* | (2006.01) | |
| *A61Q 19/08* | (2006.01) | |
| *A61K 8/73* | (2006.01) | |
| *A61K 31/726* | (2006.01) | |
| *A61Q 19/02* | (2006.01) | |

(52) U.S. Cl.
CPC .................. *A61Q 19/08* (2013.01); *A61K 8/73* (2013.01); *A61K 31/726* (2013.01); *A61Q 19/02* (2013.01); *A61K 2800/522* (2013.01)

(58) Field of Classification Search
CPC ..................................................... A61K 31/727
USPC ........................................ 514/53, 54, 56, 62
See application file for complete search history.

(56) References Cited

U.S. PATENT DOCUMENTS

| | | | |
|---|---|---|---|
| 5,902,798 A | | 5/1999 | Gouda et al. |
| 5,989,874 A | * | 11/1999 | Nakanishi et al. ........... 435/101 |
| 2007/0087039 A1 | * | 4/2007 | Gu et al. ........................ 424/442 |

FOREIGN PATENT DOCUMENTS

| | | | | |
|---|---|---|---|---|
| FR | WO 9009778 A1 | * | 9/1990 | ............... A61K 8/14 |
| JP | 63150209 A | * | 6/1988 | |
| WO | 2009/068215 A1 | | 6/2009 | |

OTHER PUBLICATIONS

Tawawa, JP 2004285166 A, Pub-date Oct. 14, 2004, Derwent - Abstract, Title—Antioxidant used in pharmaceuticals, quasi drugs and cosmetics for preventing and treating aging of skin, contains gold colloid.*
Prathiba et al., "Cutaneous wound healing: Significance of proteoglycans in scar formation", Current Science, Mar. 25, 2000, vol. 78, No. 6, pp. 1-5 (5 Pages).
Cappelletti et al., "A new electrophoretic method for the complete separation of all known animal glycosaminoglycans in a monodimensional run", Analytical Biochemistry, Nov. 1, 1979, vol. 99, Issue 2, pp. 311-315 (5 Pages).
International Application No. PCT/EP2009/062582; International Search Report and Written Opinion; Jun. 16, 2011; pp. 1-13.
Beyth et al., "Glycosaminoglycan distribution in substratum adhesion sites of aging human skin fibroblasts, including papillary and reticular subpopulations," Mechanisms of Ageing and Development, Elsevier Sequoia, Lausanne, CH, vol. 29, No. 2, Feb. 1, 1985, pp. 151-169.
Van Horssen et al., "Heparan sulphate proteoglycans in Alzheimer's disease and amyloid-related disorders," Lancet Neurology, Lancet Publishing Group, London GB, vol. 2, No. 8, Aug. 1, 2003, pp. 482-492.

* cited by examiner

*Primary Examiner* — Patrick Lewis
*Assistant Examiner* — Everett White
(74) *Attorney, Agent, or Firm* — Kilpatrick Townsend & Stockton LLP

(57) ABSTRACT

The present invention relates to cosmetological and dermatological compositions comprising heparan sulfate. The invention further discloses a process for the purification of heparan sulfate for dermatological and cosmetological applications, which process comprises the following steps: solubilization of heparan sulfate in water, adsorption on an anion exchange resin, desorption from the resin by using conditions which result in selective desorption of heparan sulfate. The cosmetological and dermatological compositions according to the invention show, inter alia, anti-age, lenitive, and whitening effect.

7 Claims, No Drawings

PROCESS FOR THE PURIFICATION OF HEPARAN SULFATE AND USE THEREOF IN COSMETOLOGICAL AND DERMATOLOGICAL PREPARATIONS

This application is a national stage of PCT/EP2009/062582, filed on Sep. 29, 2009, which claims priority to European Patent Application No. 08169547.0, filed on Nov. 20, 2008. Each of these documents is incorporated herein by reference in its entirety.

The invention relates to a new process for the purification of heparan sulfate. The present invention also relates to cosmetological and dermatological preparations making use of heparan sulfate.

Heparans are extracted from heparinoids which constitutes a by-product in the purification of heparin from pig intestinal mucosa. They are structural isomers formed during synthesis of glycosaminoglycanes (GAGs); highly sulfated and epimerised structures are typical of heparin, while highly epimerised and less N— and O— sulfated structures are typical of heparin-like structures presenting low anticoagulant activity.

It is known that endogenous proteoglycans (PG) play an important role in wound healing (V. Prathiba and S. Gupta: Cutaneous wound healing: Significance of proteoglycans in scar formation". Current Science, vol. 78, n° 6, 2000). However, the prior art does not describe the effect of administration of proteoglycans and, more specifically, of heparan sulfate in cosmetological and dermatological applications.

The present invention relates to cosmetological and dermatological preparations comprising heparan sulfate, and their use as whitening, anti-wrinkle, lenitive and anti-oxidant agent. It has been surprisingly found that heparan sulfate is effective in the treatment of the above mentioned conditions.

In a further embodiment, the invention is directed to medical devices making use of heparan sulfate in the cosmetological and dermatological field.

In another preferred embodiment, the present invention is directed to a process for the purification of heparan sulfate, which process allows the use of pure heparan sulfate in dermatological and cosmetological applications.

In a preferred embodiment, the cosmetological and dermatological preparations according to the invention make use of purified heparan sulfate. In fact, purification of heparan sulfate is an important step in order to remove residual compounds which are extracted with heparan sulfate but present different characteristics.

The purification process of the invention is characterized by the following steps: solubilization of heparan sulfate in water, adsorption on an anion exchange resin, desorption from the resin under conditions which result in selective desorption of heparan sulfate.

The anion exchange resin is preferably a strong base macroporous anion exchange resin such as, for example, Lewatit™ S 6328 A. The adsorption is performed by mixing a sufficient amount of resin beads. Preferably the amount of beads is higher than 15 g of resin per gram of heparan sulfate, more preferably is comprised between 18 and 25 g resin per gram of heparan sulfate.

After adsorption on the anion exchange resin, heparan sulfate is selectively desorbed by using an alkaline or alkaline earth metal salt, preferably an halogenide or an acetate. Examples of suitable salts are magnesium dichloride, magnesium diacetate, sodium chloride, sodium acetate, potassium chloride and potassium acetate. The pH of the salt solution is preferably comprised between 7.0 and 10.0. The concentration of the salt is important in order to achieve complete and selective desorption of heparan sulfate. A preferred range of concentration is comprised between 0.3 M and 1.0 M, more preferably between 0.5 M and 0.8 M. In fact, if the concentration of the salt is too low, the desorption of heparan sulfate is incomplete. If the concentration is too high, the desorption is not selective and, together with heparan sulfate, also highly sulfated compounds are desorbed.

After desorption from the anion exchange resin, heparan sulfate is optionally further passed on a cationic resin and on a anionic resin. An example of suitable anionic resin is Amberlite Forte IR 120™. An example of a suitable cationic resin is Amberlite Forte IRA 410™.

Purified heparan sulfate according to the invention was tested in various dermatological and cosmetological applications. More specifically, heparan sulfate was tested for whitening, lenitive and anti-age effects. In all these applications heparan sulfate showed a significant activity.

A preferred embodiment of the present invention is directed to a cosmetological composition comprising heparan sulfate.

Preferably, the cosmetological compositions according to the invention comprise from 0.01% by weight to 5% by weight of heparan sulfate, more preferably from 0.05% by weight to 2% by weight, even more preferably from 0.1% by weight to 1.0% by weight.

The molecular weight by weight (Mw) of the heparan sulfate suitable in the cosmetological and dermatological applications of the invention is preferably comprised between 6,000 and 12,000 Da.

The cosmetological compositions according to the invention optionally comprise other substances such as preservatives, emulsifiers, stabilizers, humectants, anti-oxidants, which are usually included in cosmetological and dermatological compositions.

In a preferred embodiment, the compositions according to the present invention are used as anti-age product. Many anti-age products often claim their ability to induce an increase in cell proliferation or in the protein synthesis on fibroblasts, with a linked improvement in cell firmness and thickness.

Fibroblasts are the main cell component in the connective tissue of the dermis and they are able to synthesize high amount of collagen and elastin, the main components of the dermis that play an essential role in the skin thickness and appearance. The increase in protein amount for cell stimulates the ability of fibroblasts to synthetize collagen and elastin.

Another claim for anti-aging and protective cosmetics is their activity in counteracting oxidative stress and free-radicals release in the skin. Oxidative stress is one of the main cause of aging process and is involved in the development of many serious human diseases. Exposure to UVA rays, pollutants, tobacco's smoke, as well as diet, drugs intake or pathologies can increase the level of oxidant activity in the skin cells or decrease the effectiveness of endogenous antioxidant systems. Following exposure to oxidative stress Reactive Oxygen Species (ROS) formation, damages to the cells membrane and to DNA may occur in the cell, leading to cell transformation or even death. The induction of fibroblasts proliferation and protein synthesis in dermis cells are of great concern for actives targeted to anti-age topical products.

It has been found that compositions comprising heparan sulfate are effective both as anti-wrinkle compositions and as anti-oxidant compositions.

EXPERIMENTAL

Organic sulfur, Uronic acid, Glucosamine, Optical rotation, total nitrogen and APTT were measured in accordance with the European Pharmacopeia, 4<sup>th</sup> edition. Electrophoresis was performed in accordance with R. Cappelletti et al. "A new Electrophoretic method for the separation of all Gags" Anal. Biochem. 99:311-315 (1979).

Molecular mass ($M_w$) was determined by size exclusion chromatography (European Pharmacopoeia 4<sup>th</sup> ed.: 2.2.30 and 2.2.46 for chromatography techniques and 01/2002: 0828 p. 1297 for method).

Purification of Heparan Sulfate 5 g of heparan sulfate from pig intestinal mucosa were dissolved in 200 ml of demineralised water. 90 g of Lewatit S 6238 A™ were added to the solution. The mixture was slowly stirred at room temperature for 72 h and then filtered. The filtrate was analysed and no heparan sulfate was detected.

The resin was washed, transferred in a column (diameter 3 cm, length 40 cm) and eluted with a 5% by weight solution of $MgCl_2$ at pH 8.5.

The first 300 ml are collected, after which the solution did not show presence of heparan sulfate (negative reaction to quaternary ammonium).

The solution is brought to pH=6 with a 10% solution of hydrochloric acid and heparan sulfate is precipitated by adding 600 ml of acetone. The suspension is left at 15° C. for 12 h. Then the solid is collected, dissolved in 50 ml of water and precipitated by adding 100 ml of acetone.

Heparan sulfate is then dissolved in 100 ml of water and the solution is passed over a resin Amberlite Forte IR 120™ and then over a resin Amberlite Forte IRA 410™. The eluate is neutralized by adding a 5% by weight solution of NaOH until pH 6. Water is evaporated under vacuum, the solid is filtered on a 0.45 µm filter and lyophilised. Yield: 4.12 g.

Analysis: Rotation=+50.62°. Organic S=9.07%. Uronic acid=31.97%. Glucosamine=37%. Total N=2.26%. APTT=6.31 U/mg. Mw=7538 Da (Before purification 8729 Da).

Test for Whitening Efficacy Evaluation
In Vitro Evaluation of the Bleaching Activity of a Raw Material on Cell Cultures—Test Procedure The in vitro whitening effect of HS was detected by measurement of melanin content on melanoma cells B16 (fibroblast-like cells able to produce melanin) after 6 days of contact with HS at 2 different concentrations: 0.1 mg/ml (0.01%) and 0.05 mg/ml (0.005%).

The negative control (NC) was represented by untreated cells (cell without any substance). The positive control (PC) was represented by cells treated with Hydroquinone 5 µg/ml (0.0005%). On the basis of results obtained, heparan sulphate sodium salt (HS) shows in vitro whitening effect.

TABLE I

|  | Melanin Content (µg melanin/mg protein) | % Melanin Synthesis Inhibition vs NC |
|---|---|---|
| HS (0.01%) | 41.9 | 10.3 |
| HS (0.005%) | 44.4 | 5.2 |
| PC: Hydroquinone (0.0005%) | 10.8 | 76.8 |
| NC: untreated cells | 46.8 | — |

In Vivo—Whitening Efficacy Evaluation of a Cosmetic Formulation on 20 Volunteers
Test Procedure:

The test was performed in the single blind mode. 20 volunteers (age between 40-50 years) with aged spots where present (hand, forehead, arm, face, neck). The region with aged spots was divided in two zone: one for the treatment with tested substance, one with placebo. The spots were treated for 30 consecutive days: 1 application (1 mg of substance)/die on tested area (150-200 cm<sup>2</sup>) [as per Colipa guideline].

The tested substance was an emulsion of the following composition: aqua, ethylhexyl palmitate, cetearyl alcohol, 0.9% heparan sulfate sodium salt, carbomer, acrylates/c-10-30 alkyl acrylate crosspolymer, sodium hydroxide, phenoxyethanol, propylene glycol, methylparaben, ethylparaben, propylparaben, disodium EDTA.

Placebo was an emulsion of the following composition: aqua, ethylhexyl palmitate, cetearyl alcohol, carbomer, acrylates/c-10-30 alkyl acrylate crosspolymer, sodium hydroxide, phenoxyethanol, propylene glycol, methylparaben, ethylparaben, propylparaben, disodium EDTA.

The evaluation (MI—Melanin Index by Mexameter MX 18) was made in the following way:

$T_0$—basal value, value of Melanin Index before the application of substance.

$T_{15}$—value of Melanin Index after 15 days of substance application.

$T_{30}$—final value, value of Melanin Index at the end of test (after 30 days of substance application).

TABLE II

|  | $T_0$ MI ± std dev | $T_{15}$ MI ± std dev | $T_{30}$ MI ± std dev |
|---|---|---|---|
| HS 0.9% | 229.09 ± 44.06 | 222.00 ± 58.37 | 220.81 ± 54.25 |
| Placebo | 199.89 ± 55.89 | 205.84 ± 55.95 | 215.07 ± 75.45 |

The decrease of MI (Melanin Index) in the area treated with tested substance, versus MI treated with placebo, after 30 days of application, resulted statistically relevant ($p<0.01$). Hence the Whitening Effect of tested substance (emulsion with 0.9% Heparan Sulphate sodium salt) was confirmed.

Test for Lenitive Efficacy Evaluation
In Vitro—Degranulation Test on Basophil Cells with Cosmetic Raw Materials—Test Procedure Basophil cells, when come in contact with irritant substances, give their biochemical response that is the secretion (by degranulation) of substances (such as histamine, leukotriens, proteolytic enzymes as hexosaminidase) that contribute to inflammatory events.

Inhibition in basophil cells degranulation is a measure of lenitive (anti-itching) effect of a substance. The in vitro lenitive effect of HS was detected by measurement of the release of β-hexosaminidase after 2 h of contact with HS at 4 different concentrations: 10 mg/ml (1%), 5 mg/ml (0.5%), 1 mg/ml (0.1%), 0.2 mg/ml (0.02%).

The negative control (NC) was represented by untreated cells (cells without any substance). The positive control (PC) was represented by basophil degranulation stimuli (by cross-linking the receptor FcεRI with a specific polyclonal antibody against to the α-chain stimulate the degranulation). The maximal stimulation (degranulation) is: cell treated with 1% Triton X-100. The results are reported as Optical Density (OD) at 405 nm.

TABLE III

|  | release of β-hexosaminidase OD at 450 nm |
|---|---|
| NC: untreated cells | 0.054 |
| PC: basophil degranulation | 0.117 |
| Max Stimulation | 0.377 |

TABLE III-continued

| | release of β-hexosaminidase OD at 450 nm |
|---|---|
| HS 10 mg/ml | 0.066 |
| HS 5 mg/ml | 0.059 |
| HS 1 mg/ml | 0.062 |
| HS 0.2 mg/ml | 0.061 |
| HS 10 mg/ml + PC | 0.061 |
| HS 5 mg/ml + PC | 0.055 |
| HS 1 mg/ml + PC | 0.110 |
| HS 0.2 mg/ml + PC | 0.112 |

On the basis of results obtained, heparan sulphate sodium salt (HS) shows in vitro lenitive effect.

The β-hexosaminidase "natural" level, level without any contact with irritant substance is 0.054 (OD at 450 nm). HS alone (at different concentration) has the same effect of negative control, that means leaves the cell with their "natural" level of β-hexosaminidase. This confirms that HS has no effect on basophil cells degranulation.

When the cells come in contact with an irritant substance (positive control) the value increase at 0.117, or higher to 0.377 when in contact with Triton X-100 (1%).

When the cells come in contact both with an irritant substance (positive control) and HS the level of β-hexosaminidase decrease in a dose dependent way, with best efficacy with HS at 0.5% and 1%, hence HS has a lenitive (anti-itching) effect.

In Vivo—Lenitive Efficacy Evaluation on a Cosmetic Formulation on 20 Volunteers—Short Term Test—Test Procedure The test was performed in single blind mode. 20 volunteers (age between 36-52 years) were treated on a circumscribed treated zone of 1 cm² on the back of each volunteer: one for test substance application, one for placebo application, and one for control (untreated zone). The test was performed by a single application (2 mg of substance) on tested area (1 cm²) [as per Colipa guideline]. Total time: 60 minutes after application Tested substance was an emulsion of following composition: aqua, ethylhexyl palmitate, cetearyl alcohol, 0.9% heparan sulfate sodium salt, carbomer, acrylates/c-10-30alkyl acrylate crosspolymer, sodium hydroxide, phenoxyethanol, propylene glycol, methylparaben, ethylparaben, propylparaben, disodium edta.

Placebo was an emulsion of following composition: aqua, ethylhexyl palmitate, cetearyl alcohol, carbomer, acrylates/c-10-30 alkyl acrylate crosspolymer, sodium hydroxide, phenoxyethanol, propylene glycol, methylparaben, ethylparaben, propylparaben, disodium edta.

The transient erythemagenic reaction is induced by exposure to a known amount of UVB radiation coming from a Solar Stimulator. The evaluation (EI—Erythema Index by Mexameter MX 18) were made in the following way:

$T_0$—basal value, value of Erythema Index after UVB radiation and before the application of substance $T_{15}$—value of Erythema Index after 15 minutes from substance application $T_{30}$—value of Erythema Index after 30 minutes from substance application $T_{60}$—value of Erythema Index after 60 minutes from substance application

TABLE IV

| | $T_0$ EI ± std dev | $T_{15}$ EI ± std dev | $T_{30}$ EI ± std dev | $T_{60}$ EI ± std dev |
|---|---|---|---|---|
| Tested Substance | 455.75 ± 64.63 | 439.55 ± 82.67 | 421.59 ± 72.31 | 406.39 ± 77.06 |
| Placebo | 453.21 ± 71.50 | 430.26 ± 76.22 | 415.69 ± 67.42 | 415.79 ± 75.18 |

TABLE V

| | $T_0$ vs $T_{15}$ | $T_0$ vs $T_{30}$ | $T_0$ vs $T_{60}$ |
|---|---|---|---|
| Tested Substance | −4.19 | −8.29 | −11.24 |
| Placebo | −5.36 | −8.29 | −8.58 |

The decrease of EI (Erythema Index) in the area treated with tested substance, versus EI treated with placebo, after 60 minutes from application, resulted statistically relevant ($p<0.1$), and is statistically relevant ($p<0.01$) the decrease after 60 minutes versus basal value. Hence the Lenitive (redness reduction) Effect of tested substance (emulsion with 0.9% Heparan Sulphate sodium salt) has been confirmed.

Test for Anti-Wrinkle Efficacy Evaluation

In vitro Evaluation of the anti-ageing activity of cosmetic products through the investigation of their anti-oxidant and protective activity against UVA on human keratinocytes cell cultures.

Test Procedure

The antioxidant effect of HS is detected by measurement of reduction of free radicals as Reactive Oxygen Species (ROS) after exposure to 3 different UVA irradiation for 1 minute and 30 seconds (1' 30"), for 3 minutes (3') and for 4 minutes and 30 seconds (4' 30"), with HS at 7 different concentrations: 0.031 mg/ml (0.0031%), 0.063 mg/ml (0.0063%), 0.125 mg/ml (0.0125%), 0.250 mg/ml (0.0250%), 0.500 mg/ml (0.0500%), 1.000 mg/ml (0.1000%) and 9.000 mg/ml (0.9000%). The negative control (NC) was: untreated cells (cells without any substance). The positive control (PC) was: Vitamin C (0.15 mg/ml) (0.015%).

Table VI shows the results obtained. It is evident that heparan sulphate sodium salt (HS) shows in vitro antioxidant effect. The efficacy of HS at 0.1% concentration is comparable or even higher than the efficacy of Vitamin C. The efficacy of HS is higher that Vitamin C even at prolonged exposure to UVA radiation (4' 30").

TABLE VI

| | Exposure | Heparan Sulphate Sodium Salt mg/ml | | | | | | | Vit C mg/ml |
|---|---|---|---|---|---|---|---|---|---|
| | | 9.000 | 1.000 | 0.500 | 0.250 | 0.125 | 0.063 | 0.031 | 0.15 |
| ROS Inhibition % | 1'30" UVA | 30.7 | 38.7 | 30.6 | 28.0 | 23.5 | 25.4 | 25.3 | 33.5 |
| | 3'00" UVA | 31.6 | 35.7 | 29.1 | 22.9 | 14.2 | 21.8 | 20.1 | 31.4 |
| | 4'30" UVA | 26.3 | 30.4 | 24.7 | 18.1 | 10.3 | 13.7 | 6.2 | 12.7 |

In Vitro—Mitogenic Activity Evaluation of a Raw Material Test Procedure:

The mitogenic effect of HS is detected by measurement of fibroblast cells proliferation, measurement of protein synthesis after exposure for 48 hours and 72 hours, using HS at 2 different concentrations: 0.1 mg/ml (0.01%) and 0.05 mg/ml (0.005%). The negative control (NC) is represented by untreated cells, the positive control (PC) is: EGF (Epidermal Growth Factor) (10 µg/ml) (0.001%).

TABLE VII

| | % cell proliferation vs NC | |
|---|---|---|
| | 48 h | 72 h |
| PC: EGF (10 µg/ml) (0.001%) | 112.5 | 121.6 |
| HS 0.1 mg/ml (0.01%) | 110.5 | 118.1 |
| HS 0.05 mg/ml (0.005%) | 106.7 | 118.2 |
| | % protein synthesis vs NC | |
| | 48 h | 72 h |
| PC: EGF (10 µg/ml) (0.001%) | 116.6 | 119.0 |
| HS 0.1 mg/ml (0.01%) | 103.1 | 113.2 |
| HS 0.05 mg/ml (0.005%) | 110.2 | 120.4 |

On the basis of results obtained, heparan sulphate sodium salt (HS) shows in vitro cell proliferation and protein synthesis efficacy. The highest effect (18.2% for cell proliferation and 20.4% for protein synthesis) is observed after 72 hour from exposure at 0.05 mg/ml.

The invention claimed is:

1. A cosmetological and dermatological composition consisting of heparan sulfate and one or more of the following ingredients: preservatives, emulsifiers, stabilizers, humectants, and anti-oxidants, wherein the heparan sulfate has a molecular weight between 6,000 and 12,000 Da and wherein the heparan sulfate is present between 0.5% by weight and 5% by weight heparan sulfate based on the total weight of the cosmetological and dermatological composition.

2. The composition according to claim 1, wherein the heparan sulfate is present between 0.5% by weight and 2% by weight-based on the total weight of the cosmetological and dermatological composition.

3. The composition according to claim 1, wherein the heparan sulfate is present between 0.5% by weight and 1% by weight-based on the total weight of the cosmetological and dermatological composition.

4. A cosmetological and dermatological composition consisting of heparan sulfate and one or more of the following ingredients: preservatives, emulsifiers, stabilizers, humectants, and anti-oxidants, wherein the heparan sulfate is present between 0.5% by weight and 5% by weight based on the total weight of the cosmetological and dermatological composition.

5. The composition according to claim 4, wherein the heparan sulfate has a molecular weight between 6000 and 12,000 Da.

6. The composition according to claim 4, wherein the heparan sulfate is present between 0.5% by weight and 2% by weight-based on the total weight of the cosmetological and dermatological composition.

7. The composition according to claim 4, wherein the heparan sulfate is present between 0.5% by weight and 1% by weight-based on the total weight of the cosmetological and dermatological composition.

* * * * *